(12) United States Patent
Tan et al.

(10) Patent No.: US 12,017,076 B2
(45) Date of Patent: *Jun. 25, 2024

(54) BLOOD PUMP WITH CAPABILITY OF ELECTROCARDIOGRAM (EKG) MONITORING, DEFIBRILLATION AND PACING

(71) Applicant: ABIOMED, Inc., Danvers, MA (US)

(72) Inventors: Qing Tan, Danvers, MA (US); Ahmad El Katerji, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/981,039

(22) Filed: Nov. 4, 2022

(65) Prior Publication Data

US 2023/0158309 A1 May 25, 2023

Related U.S. Application Data

(63) Continuation of application No. 16/910,690, filed on Jun. 24, 2020, now Pat. No. 11,524,165.
(Continued)

(51) Int. Cl.
*A61N 1/362* (2006.01)
*A61M 60/13* (2021.01)
(Continued)

(52) U.S. Cl.
CPC .......... *A61N 1/3629* (2017.08); *A61M 60/13* (2021.01); *A61M 60/139* (2021.01);
(Continued)

(58) Field of Classification Search
CPC ................. A61B 5/0215; A61B 5/287; A61M 2205/3365; A61M 2205/502;
(Continued)

(56) References Cited

U.S. PATENT DOCUMENTS

| 4,014,317 A | 3/1977 | Bruno |
|---|---|---|
| 9,352,159 B2 | 5/2016 | Fishel |

(Continued)

FOREIGN PATENT DOCUMENTS

| CN | 102458572 A | 5/2012 |
|---|---|---|
| CN | 107249665 A | 10/2017 |

(Continued)

OTHER PUBLICATIONS

Partial Search Report and Provisional Opinion for International Application No. PCT/US2020/039339 dated Sep. 23, 2020 (10 pages).

(Continued)

*Primary Examiner* — Jon Eric C Morales
(74) *Attorney, Agent, or Firm* — Botos Churchill IP Law LLP

(57) ABSTRACT

A blood pump system includes a catheter, a pump housing disposed distal of a distal end of the catheter, a rotor positioned at least partially in the pump housing, a controller, and an electrode coupled a distal region of the blood pump. The electrode can be used to sense electrocardiogram (EKG) signals and transmit the signals to a controller of the blood pump. The operation of the blood pump can be adjusted based on the EKG signal and on cardiac parameters derived from the EKG signal. Further, the controller can determine a need for defibrillation or pacing of the patient's heart based on the signal and can administer treatment with electrical shocks to the heart via the electrode coupled to the blood pump. The use of an electrode with a blood pump already in place in the heart allows for more efficient and safer treatment of serious cardiac conditions.

20 Claims, 8 Drawing Sheets

Related U.S. Application Data

(60) Provisional application No. 62/868,403, filed on Jun. 28, 2019.

(51) Int. Cl.
*A61M 60/139* (2021.01)
*A61M 60/216* (2021.01)
*A61M 60/414* (2021.01)
*A61M 60/416* (2021.01)
*A61M 60/531* (2021.01)
*A61M 60/857* (2021.01)
*A61N 1/365* (2006.01)
*A61N 1/39* (2006.01)

(52) U.S. Cl.
CPC ........ *A61M 60/216* (2021.01); *A61M 60/414* (2021.01); *A61M 60/416* (2021.01); *A61M 60/531* (2021.01); *A61M 60/857* (2021.01); *A61N 1/365* (2013.01); *A61N 1/3962* (2013.01); *A61M 2205/3365* (2013.01); *A61M 2205/502* (2013.01); *A61M 2230/04* (2013.01)

(58) Field of Classification Search
CPC .............. A61M 2230/04; A61M 60/13; A61M 60/139; A61M 60/216; A61M 60/237; A61M 60/414; A61M 60/416; A61M 60/515; A61M 60/531; A61M 60/538; A61M 60/816; A61M 60/857; A61N 1/3629; A61N 1/365; A61N 1/3962
See application file for complete search history.

(56) References Cited

U.S. PATENT DOCUMENTS

| | | | |
|---|---|---|---|
| 9,717,914 B2 | 8/2017 | Min et al. | |
| 9,717,922 B2 | 8/2017 | Amir et al. | |
| 9,814,889 B2 | 11/2017 | Strommer et al. | |
| 10,050,476 B2 | 8/2018 | Strommer et al. | |
| 10,170,944 B2 | 1/2019 | Strommer et al. | |
| 10,293,174 B2 | 5/2019 | Amir et al. | |
| 10,434,316 B2 | 10/2019 | Kelley et al. | |
| 10,610,693 B2 | 4/2020 | Strommer et al. | |
| 11,524,165 B2 * | 12/2022 | Tan ..................... | A61M 60/216 |
| 2007/0287880 A1 | 12/2007 | Ovil et al. | |
| 2010/0268295 A1 | 10/2010 | Imran et al. | |
| 2011/0178361 A1 | 7/2011 | Yomtov | |
| 2012/0310037 A1 | 12/2012 | Choi et al. | |
| 2015/0343228 A1 | 12/2015 | Strommer et al. | |
| 2016/0038751 A1 | 2/2016 | Broder et al. | |
| 2016/0045736 A1 | 2/2016 | Fishel | |
| 2016/0166837 A1 | 6/2016 | Strommer et al. | |
| 2016/0175600 A1 | 6/2016 | Amir et al. | |
| 2016/0331980 A1 | 11/2016 | Strommer et al. | |
| 2017/0246459 A1 | 8/2017 | Kelley et al. | |
| 2017/0266454 A1 | 9/2017 | Amir et al. | |
| 2017/0348471 A1 | 12/2017 | Goto et al. | |
| 2018/0028823 A1 | 2/2018 | Strommer et al. | |
| 2018/0078159 A1 | 3/2018 | Edelman et al. | |
| 2018/0078774 A1 | 3/2018 | Strommer et al. | |
| 2018/0323652 A1 | 11/2018 | Strommer et al. | |
| 2019/0126051 A1 | 5/2019 | Strommer et al. | |
| 2019/0262621 A1 | 8/2019 | Amir et al. | |
| 2019/0381329 A1 | 12/2019 | Fishel et al. | |
| 2020/0038567 A1 | 2/2020 | Siess et al. | |
| 2020/0139108 A1 | 5/2020 | Strommer et al. | |
| 2021/0260361 A1 | 8/2021 | Charafeddine et al. | |

FOREIGN PATENT DOCUMENTS

| | | |
|---|---|---|
| EP | 3287154 A1 | 2/2018 |
| WO | 2018073150 A1 | 4/2018 |

OTHER PUBLICATIONS

Communication Pursuant to Article 94(3) EPC for European Application No. 20739548.4 dated Mar. 6, 2024.
Office Action dated Mar. 1, 2024 for JP Appln. No. 2021-577251, (8 pp.).

* cited by examiner

BLOOD PUMP WITH CAPABILITY OF ELECTROCARDIOGRAM (EKG) MONITORING, DEFIBRILLATION AND PACING

CROSS-REFERENCE TO RELATED APPLICATIONS

The present application is a continuation of U.S. application Ser. No. 16/910,690, filed Jun. 24, 2020 and published as U.S. Pub. 2020/0405929 A1, now U.S. Pat. No. 11,524,165, which claims priority to U.S. Provisional Application No. 62/868,403, filed Jun. 28, 2019, the entire disclosures of which are incorporated by reference herein.

BACKGROUND

Cardiovascular diseases are a leading cause of morbidity, mortality, and burden on healthcare around the world. A variety of treatment modalities have been developed for cardiovascular disease, ranging from pharmaceuticals to mechanical devices and finally transplantation. Temporary cardiac support devices, such as ventricular assist devices, provide hemodynamic support, and facilitate heart recovery. Some intracardiac heart pump assemblies can be introduced into the heart either surgically or percutaneously and used to deliver blood from one location in the heart or circulatory system to another location in the heart or circulatory system. For example, when deployed in the heart, an intracardiac pump can pump blood from the left ventricle of the heart into the aorta, or pump blood from the inferior vena cava to the pulmonary artery. Intracardiac pumps can be powered by a motor located outside of the patient's body or a motor located inside the patient's body. Some intracardiac blood pump systems can operate in parallel with the native heart to supplement cardiac output and partially or fully unload components of the heart. Examples of such systems include the IMPELLA® family of devices (Abiomed, Inc., Danvers MA).

Among the population of patients who require hemodynamic support by a mechanical circulatory support system, such as an intracardiac blood pump, it is common to experience heart arrhythmia, or irregular heartbeats. When the arrhythmia is severe, it may be necessary to correct the heart rhythm with a pacing or defibrillation device.

In a critical care setting, a patient suffering from life-threatening cardiac arrhythmia or dysrhythmia is often defibrillated by a manual external defibrillator or automated external defibrillator to deliver a dose of electric current to the heart through the application of large pads or electrodes to the patient's skin to depolarize the heart and end the irregular heartbeat. Defibrillation is used only when specific kinds of arrhythmias are detected, and improper defibrillation can cause dangerous dysrhythmia and other injuries.

Adjustments to the heart's pacing are similarly addressed in critical care settings by use of transcutaneous, or external, pacing. In transcutaneous pacing, a clinician typically uses pads or electrodes placed on the patient's chest to provide pulses of electrical current to stimulate contraction of the heart. Pacing is required when an abnormally slow heartrate is detected, called bradycardia.

In situations in which pacing or defibrillation are required, the clinician must first recognize that treatment is required, diagnose the cardiac irregularity, and determine the proper treatment. When defibrillation is indicated, the clinician must then place the electrodes or pads on the patient, determine the voltage and timing for the electrical shock, and administer the electric shock to the patient. When pacing is indicated, the clinician places the electrodes or pads on the patient, and selects a heart rate and adjusts the current to the appropriate level.

Delay in administering the pacing or defibrillation to a patient when necessary can be detrimental to a patient's condition and may result in lowered survival rate. Further, defibrillation and transcutaneous pacing may be uncomfortable for the patient. Unfortunately, because electrical shocks for defibrillation and pacing in a critical care or emergency setting are most often applied externally, high amounts of electrical charge are required, sometimes resulting in serious injury to the patient. Accordingly, there is a need for new technologies providing efficient and safe pacing and defibrillation to patients.

SUMMARY

The methods, systems, and devices described herein enable use of a circulatory assist device including an electrode with transmission, sensing, and electrical charge delivery capabilities to provide circulatory support, detect an electrocardiogram (EKG) signal, and detect and react to changes in heart function based on the EKG signal by changing an amount of support provided by the device and providing defibrillation and pacing of the heart when necessary.

By integrating a pacing and defibrillation function into a circulatory assist device, a system becomes available for treating arrhythmia in real-time during circulatory assist, thereby reducing treatment delay and severity of the arrhythmia indication. An electrode (or other similar device for sensing or stimulation, or both) may be implemented on the circulatory assist device (e.g., a blood pump) for pacing and defibrillation. Such a device may also be utilized as an EKG (sometimes also called ECG) electrode. The EKG data can be provided by the electrode to the controller of the circulatory assist device to provide additional information about the patient's condition to clinicians. The EKG data can further enhance the ability of the assist device controller to quickly identify and respond to cardiac events or changes in cardiac function.

In general, a mechanical circulatory support system includes a mechanical circulatory support device, a controller communicatively coupled to the mechanical circulatory support device and designed to control a level of support provided by the mechanical circulatory support device, and an electrode coupled to the mechanical support device. Mechanical circulatory support systems may include one or more of an intravascular blood pump, an extracorporeal membrane oxygenation (ECMO) device, an intra-aortic balloon pump, a left-ventricular assist device (LVAD) implanted surgically, or a percutaneous expandable blood pump positioned in the right or left heart. In an aspect, the circulatory assist device includes an intravascular blood pump system with a catheter having a proximal end and a distal end, a blood pump disposed distal of the distal end of the catheter, and an electrode coupled to a distal region of the blood pump.

In another aspect, an intravascular blood pump system includes an intravascular blood pump, a controller, and an electrode coupled to the intravascular blood pump. The intravascular blood pump includes a catheter having a proximal end and a distal end, a pump housing disposed distal of the distal end of the catheter, and a rotor positioned at least partially in the pump housing, the rotor designed to be rotatably driven. The controller is communicatively coupled to the intravascular blood pump and is designed to control a level of support provided by the intravascular blood pump by controlling a speed of the rotor.

In another aspect, a method of providing circulatory support with a circulatory assist device, such as an intravascular blood pump, includes placing the device (e.g., the intravascular blood pump) within vasculature of a patient and operating the intravascular blood pump by rotating a rotor within a pump housing at a pump speed. The method further includes measuring an EKG signal within the vasculature using an electrode coupled to the intravascular blood pump and adjusting the pump speed of the rotor based on the EKG signal.

In another aspect, a method for measuring an EKG signal while providing circulatory support includes placing a circulatory support device within vasculature of a patient, where the circulatory support device includes an electrode coupled to the circulatory support device. The method also includes operating the circulatory support device within the vasculature of the patient, and measuring an EKG signal within the vasculature using the electrode.

In another aspect, a method for providing pacing of a patient's heart while providing circulatory support includes placing a circulatory support device within vasculature of a patient, where the circulatory support device includes an electrode coupled to the circulatory support device. The method further includes operating the circulatory support device within the vasculature, measuring an EKG signal within the vasculature using the electrode, determining a need for pacing of the patient's heart based on the EKG signal, and transmitting an electrical charge for delivery at the electrode to pace the patient's heart.

In another aspect, a method for providing defibrillation of a patient's heart while providing circulatory support includes placing a circulatory support device within vasculature of a patient, where the circulatory support device includes an electrode coupled to the circulatory support device. The method further includes operating the circulatory support device within the vasculature, measuring an EKG signal within the vasculature using the electrode, determining a need for defibrillation of the patient's heart based on the EKG signal, and transmitting an electrical charge for delivery at the electrode to defibrillate the patient's heart.

DETAILED DESCRIPTION

Figure 1:
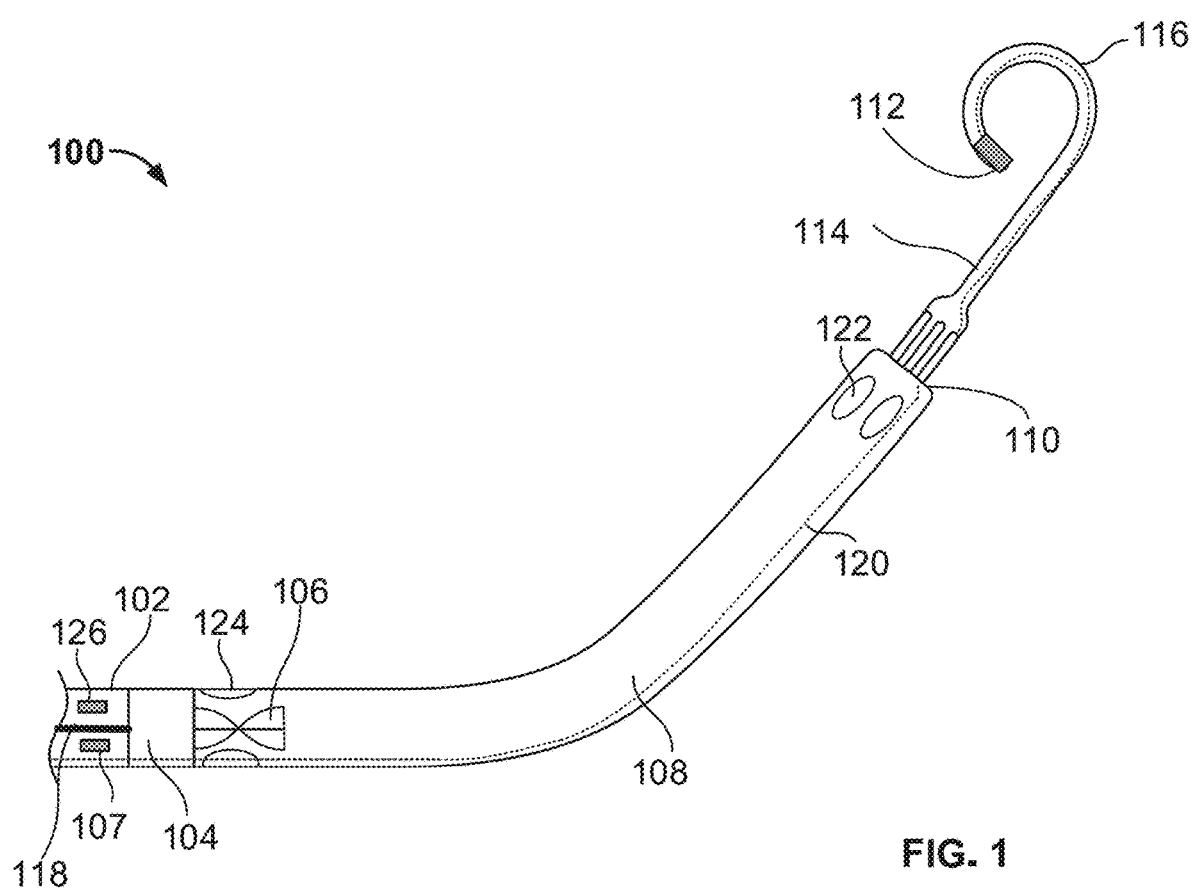
FIG. 1. shows an exemplary blood pump system including an electrode according to aspects of the disclosure.

FIG. 1. shows an exemplary blood pump system 100 according to aspects of the disclosure which includes a catheter 102, a pump housing 104, a rotor 106, a driveshaft (or drive cable) 118, a cannula 108, a flexible projection 114, an electrode 112, and a reference electrode 107. The pump housing 104 of the blood pump system 100 is coupled to a distal end of a catheter 102. The rotor 106 is coupled to the driveshaft 118, and is positioned within the pump housing 104. In addition, as shown in the example of FIG. 1, the rotor 106 may also extend beyond the distal end of the pump housing 104 into the proximal end of cannula 108. In some aspects of the technology, the driveshaft 118 may extend through the catheter 102, and may be configured to rotatably drive the rotor 106 via a motor located outside of the patient's body. In some aspects of the technology, the rotor 106 may be driven by a motor located inside the patient's body, such as by a motor located within the pump housing 104. The cannula 108 extends from a distal end of the pump housing 104. The blood pump system 100 includes inlet apertures 122 and outlet apertures 124. While the outlet apertures 124 are shown in FIG. 1 as being formed in the proximal end of cannula 108, they may alternatively be formed in the wall of pump housing 104. Likewise, while the inlet apertures 122 are shown in FIG. 1 as being formed in the distal end of cannula 108, they may alternatively be formed in a blood inflow cage structure attached to the distal end of cannula 108 (which may be considered a part of cannula 108).

The flexible projection 114 extends from a distal end 110 of the cannula 108. The electrode 112 is coupled to the blood pump system 100. The blood pump system can be utilized in a right heart configuration or a left heart configuration, as will be described below in FIGS. 2 and 3, respectively.

The electrode 112 is positioned at the distal end of the cannula 108, for example, on the flexible projection 114. The flexible projection 114 may be implemented as a pigtail or as a straight projection from the distal end of the cannula 108. In some implementations, the flexible projection 114 includes a ball or sphere. A distal portion 116 of the flexible projection 114 may provide guidance and positioning of the blood pump system 100 within the heart. For example, the flexible projection may be used to space the inlet apertures 122 of the blood pump system 100 from a wall of the heart, or to guide the blood pump system 100 through the vasculature.

Electrical wires 120 are positioned in the blood pump system 100 connecting the electrode 112 to the controller (not shown). The electrical wires 120 may be embedded in a wall of the cannula 108, and may extend through the catheter 102 to the controller. The blood pump system 100 may further include a pressure sensor and/or optical sensor 126 located on the catheter 102 as shown, or located elsewhere on the blood pump system 100. The electrical wires 120 coupled to the electrode 112 may follow the same path through the catheter 102 as electrical wires, pressure lines, and optical fibers coupled to the pressure sensor and/or optical sensor 126 of the blood pump system 100. The electrical wires 120 provide the electrical connection and power supply from the controller to the electrode 112. The electrode 112 can be designed to function as a pacing and/or defibrillation electrode 112 equipped to transmit an electrical charge to the heart, and is also functional as a sensing electrode 112 to measure an EKG signal and transmit the signal to the controller through the electrical wires 120. The function of the controller and the electrode 112 together will be described in greater detail below with reference to FIGS. 2 and 3.

In the example of FIG. 1, the reference electrode 107 is positioned on the catheter 102 that connects the blood pump system 100 to the controller and near the distal end of catheter 102 so that it is positioned within the patient's vasculature. However, the reference electrode 107 may alternatively be positioned external to the body of the patient, e.g., on the patient's skin. This reference electrode 107 may be connected to the controller by an electrical wire, which may be the same electrical wires 120 connecting the electrode 112 to the controller through the catheter 102. The measured EKG signal reflects the difference in electrical potential between the electrode 112 on the blood pump system 100 and the reference electrode 107. When the pacing or defibrillation therapy is administered, the electrical voltage is delivered between the electrode 112 mounted on the blood pump system 100 and the reference electrode 107.

By providing the electrode 112 for sensing, pacing, and defibrillation directly on the blood pump system 100, no additional catheter is needed for EKG sensing, and external pacing and defibrillation methods are unnecessary. The time delay in providing treatment for severe arrhythmia is decreased relative to conventional methods utilizing external manual defibrillation or transcutaneous pacing, because the required electrode 112 is already in a position to provide an electrical charge to the heart. Because the electrode 112 is within the heart and able to provide the electrical shock directly to the heart tissue, the amount of electrical charge required may be decreased, providing a more efficient system and decreasing the chance of causing additional injuries which can occur with external defibrillation or pacing which require larger currents and electrical charges.

Figure 2:
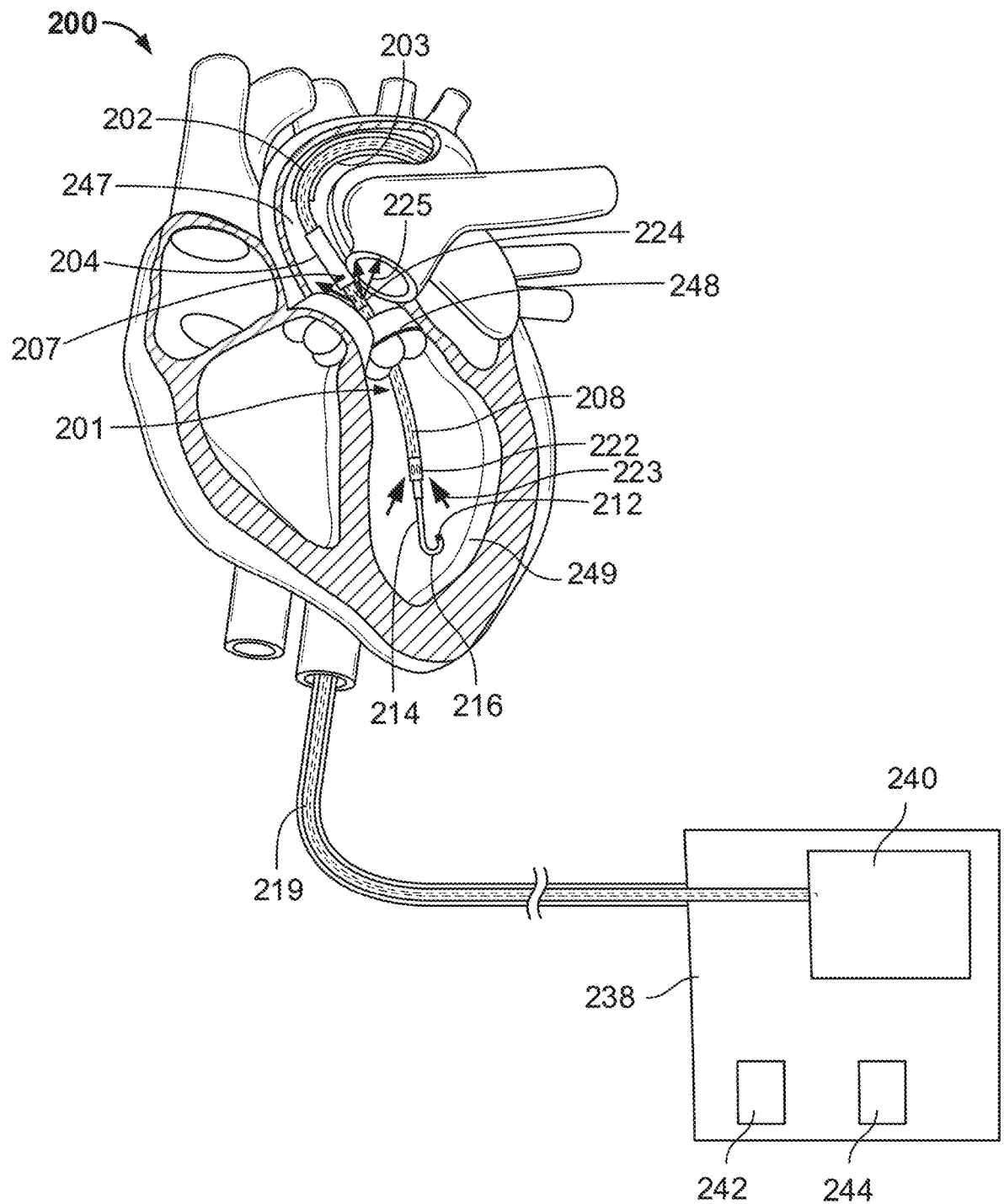
FIG. 2 shows an exemplary blood pump system including an electrode positioned in the left heart according to aspects of the disclosure.

FIG. 2 shows an exemplary blood pump system 200 according to aspects of the disclosure which includes an electrode 212 positioned on a blood pump 201 in the left heart. The blood pump system 200 includes a blood pump 201 and a controller 238. The blood pump 201 includes a cannula 208, pump 204, at least one inlet aperture 222 through which blood flows into the cannula 208 (as indicated by arrows 223), at least one outlet aperture 224 through which blood exits the cannula 208 (as indicated by arrows 225), a reference electrode 207, a catheter 202, and a flexible projection 214 at a distal end of the cannula 208. For example, the blood pump 201 including the electrode 212 may be the blood pump system 100 of FIG. 1. The blood pump 201 may be an IMPELLA® device, or any other suitable blood pump. Here as well, the at least one outlet aperture 224 may be formed in the proximal end of cannula 208 or may be a formed in a pump housing structure attached to the proximal end of cannula 208. Likewise, the at least one inlet aperture 222 may be formed in the distal end of cannula 208 or may be formed in a blood inflow cage structure attached to the distal end of cannula 208 (which may be considered a part of cannula 208).

The pump 204 is coupled to a first catheter 202 which extends through a second catheter 203. Both the first catheter 202 and the second catheter 203 extend through the vasculature to attach the blood pump 201 to the controller 238. The first catheter 202 may be movable within the second catheter 203. The second catheter 203 is a non-rotating catheter. In some implementations, the blood pump 201 can be withdrawn into the second catheter 203 for insertion or removal of the blood pump 201 through the vasculature. In some implementations, the blood pump 201 can be compressed by being withdrawn into the second catheter 203.

The electrode 212 is positioned on the flexible projection 214 as shown, or elsewhere at the distal end of the blood pump 201 such as the distal end of the cannula 208. The blood pump 201 is positioned across the aortic valve 248 so that at least one inlet aperture 222 is in the left ventricle 249 and at least one outlet aperture 224 is in the aorta 247. The electrode 212, whether on the flexible projection 214 or a distal end of the cannula 208, is positioned within the left ventricle 249, where it can be used to administer electrical shocks to the heart for defibrillation or pacing if required. The electrode 212, may further be positioned on a most distal portion of the flexible projection 216. The flexible projection 214 may serve to space the inlet aperture 222 from the walls of the left ventricle 249. The electrode 212 need not be in contact with the heart tissue, because the blood within the heart is also conductive. The reference electrode 207 is positioned on the catheter 202 that connects the blood pump 201 to the controller 238 and near the blood pump 201 so that it is positioned within the patient's vasculature. The reference electrode 207 may alternatively be positioned external to the body of the patient on the skin. This reference electrode 207 may be connected to the controller 238 by an electrical wire, which may be the same electrical wires 219 connecting the electrode 212 to the controller 238 through the catheter 202. The measured EKG signal reflects the difference in electric potential between the electrode 212 on the blood pump 201 and the reference electrode 207. When the pacing or defibrillation therapy are administered, the electrical voltage is delivered between the electrode 212 mounted on the blood pump 201 and the reference electrode 207.

The controller 238 includes a processor 240 (or a set of one or more processors 240) for controlling operation of the blood pump 218 and which is communicatively coupled to the electrode 212. The controller 238 also includes memory 242 and display 244 (which may further include one or more audio devices such as speakers, chimes, etc.). For example, the controller 238 may be the Automated Impella Controller (AIC) of Abiomed, Inc. or any other suitable controller. The electrode 212 is coupled to the controller 238 by electrical wires 219 which extend through the cannula 208 and first catheter 202. As described above with regard to FIG. 1, the electrical wires 219 may be embedded in a wall of the cannula 208 and extend through the catheter 202 to the controller 238. The electrical wires 219 provide the electrical connection and power supply from the controller 238 to the electrode 212. In some implementations, the electrode 212 may be coupled to a wireless transmitter and may be designed to function on the blood pump system 200 without electrical wires 219 directly connecting the electrode 212 to the controller 238.

The electrode 212 functions as described above with regard to FIG. 1 to measure the EKG signals within the heart, and to provide electrical charges to the heart for pacing and defibrillation if necessary. The electrode 212 transmits an EKG signal to the controller 238. The controller 238 may display the signal to a clinician on the display 244 to allow the clinician to diagnose arrhythmias. The controller 238 may also record the EKG signals in the memory 242. The controller 238 may also include, in the processor 240 and/or memory 242, software used to analyze the EKG signal to detect and diagnose arrhythmias, and may further be configured to alert the clinician to detected arrhythmias and suggested treatments determined by the processor 240 on the display 244. Because the electrode 212 is coupled to the blood pump 201 already located in the heart, the administration of treatment by pacing or defibrillation is rendered much more efficient. For example, the clinician may transmit an electrical shock to the heart via the electrode 212 by entering a command on the controller 238. Additionally, the controller 238 may include software that determines an appropriate electrical voltage, timing, and/or heartrate and current to be administered and prompts the clinician to administer the treatment. Analyzing the EKG signal at the controller 238 enables a much quicker response to arrhythmias and cardiac events than are currently possible using external manual defibrillation and pacing.

After the controller 238 receives the EKG signal from the electrode 212, the controller 238 generates the EKG signal and/or the cardiac characteristics derived from the signal for display on the display 244. Displaying the EKG signal to the clinician allows the clinician to easily see the morphology and timing of the EKG waves for diagnostic purposes.

Based on the EKG information transmitted by the electrode 212, the controller 238 can make determinations about the cardiac function of the patient that aid in the operation of the blood pump 201. The controller 238 receives the digital signal comprising the EKG signal at the processor 240 and uses the information along with other signals and data available to the controller 238 to extract cardiac parameters and characteristics indicative of cardiac function.

The controller 238 extracts cardiac parameters from the EKG data transmitted by the electrode 212 and uses the data to make determinations about the effect of the support provided by the blood pump 201. Based on the EKG data transmitted to the controller 238, the controller can extract cardiac parameters such as left ventricular end diastolic pressure (LVEDP) which can be used to better understand cardiac function. The LVEDP indicates the pressure in the left ventricle of the heart at the end of diastole and is a critical value in determining patient health and cardiac function that can be derived from signal processing from pressure and motor characteristics of the blood pump. A low LVEDP indicates a healthy patient, while a higher LVEDP can be an indication of disease or illness.

For example, the EKG signal provided to the controller is a tracing of an R-wave. The top of the R-wave indicates the timing in the cardiac cycle when the pressure measurement is indicative of the LVEDP. Because the EKG signal makes the timing of the pressure measurement clearer, the controller 238 can extract information about the timing of the LVEDP in the cardiac cycle from the EKG signal and the LVEDP measurement can be taken at the precise timing at which the LVEDP occurs in the cycle. With the information from the EKG signal, the LVEDP can be determined more accurately.

Alternatively or additionally, the EKG signal can be used to determine appropriate timing in the cardiac cycle for measurements used to determine other cardiac parameters such as left ventricular volume, aortic pulse pressure, mean aortic pressure, pump flow, pressure gradient, heart rate, cardiac output, cardiac power output, native cardiac output, native cardiac power output, cardiac contractility, cardiac relaxation, fluid responsiveness, volume status, and cardiac unloading or recovery index.

The controller 238 uses the EKG signal to time the measurement of aortic pressure to accurately estimate the LVEDP (or other cardiac parameter) based on the pressure measurement and motor parameters, and presents the information to the clinician on the display 244. The controller can also further process the data to determine whether circulatory support provided by the blood pump 201 should be altered to provide more or less support to the patient. With the accurate measurement of the LVEDP using the EKG signal from the electrode 212, the controller 238 can be more responsive to changes in cardiac function. In particular, the controller 238 can use the extracted cardiac parameters, including LVEDP, to determine whether circulatory support should be increased or decreased, and can alter the support in response by changing the speed of the rotor or prompting a clinician to do so.

In some implementations, the controller 238 can be used to automate operation of the blood pump 201 and the support provided by the blood pump 201. The EKG signals provided to the controller 238 allow the controller 238 to better anticipate and quickly identify changes in cardiac function. Based on the EKG signal and cardiac parameters extracted from the EKG and other signals available to the controller 238, the controller 238 may adjust the rotor speed in order to provide more or less support. Alternatively, the controller 238 may prompt a clinician to change a speed of the rotor by displaying a recommendation on the display 244.

The controller 238 may also be able to use the EKG signal to detect premature ventricular contraction, when the heart skips a beat, and other cardiac conditions. The controller 238 can then alert a clinician and can adjust support as necessary or provide additional treatment options using the electrode 212 incorporated in the blood pump 201.

The controller 238 may also use the EKG signal to determine whether irregular heartbeats are present indicating that there is a need for pacing or defibrillation of the heart. The need for pacing may be determined by comparison of an EKG signal to a reference signal, comparing a current EKG signal to a historical EKG signal of the patient, or comparison of a number of heart beats per minute extracted from the EKG signal to a threshold, for example 60 beats per minute (BPM) for an adult. Detection of an irregular heartbeat, or too fast of a heartbeat, may indicate a cardiac dysrhythmia for which defibrillation is an appropriate treatment, such as ventricular fibrillation or pulseless ventricular tachycardia. An irregular heartbeat requiring defibrillation may be determined by comparison of the EKG signal to a reference signal, comparison of a current EKG signal to a historical EKG signal of the patient, comparison of a number of heart beats per minute extracted from the EKG signal to a threshold value, or comparison of the EKG signal to a reference rhythm of heartbeats associated with cardiac arrest. Alternatively, the irregularity may be determined by software programmed to identify irregular or too-fast heartbeats, or by a machine-learning algorithm trained to identify these events.

When a need for pacing or defibrillation is detected, the controller 238 may alert a clinician by displaying a warning or recommendation on the display 244. The controller 238 may further make a determination of which of pacing or defibrillation is required, and a determination of the appropriate parameters for the electrical shock that should be administered as treatment of the condition. For example, the timing and voltage of the electric shock to be administered to defibrillate the heart may be determined by the controller 238. In some implementations, the timing and voltage of the electric shock is input into a system by a clinician, or is determined by the controller 238 and approved by a clinician. In other implementations, the timing, current, heart rate and other parameters of the electrical charge are determined by the controller 238. In some implementations, the relevant parameters related to pacing of the heart are input into a system by a clinician, or may be determined by the controller 238 and approved by a clinician. The dose of electric current is then delivered to the heart through the electrode 212 to depolarize the heart muscle and end the arrhythmia. Because the electrode 212 is already in place and the charge can be delivered directly to the heart, defibrillation or pacing of the heart using the blood pump system 200 including an electrode 212 is more efficient and less dangerous than treatment using a manual external defibrillator or transcutaneous pacing device.

Figure 3:
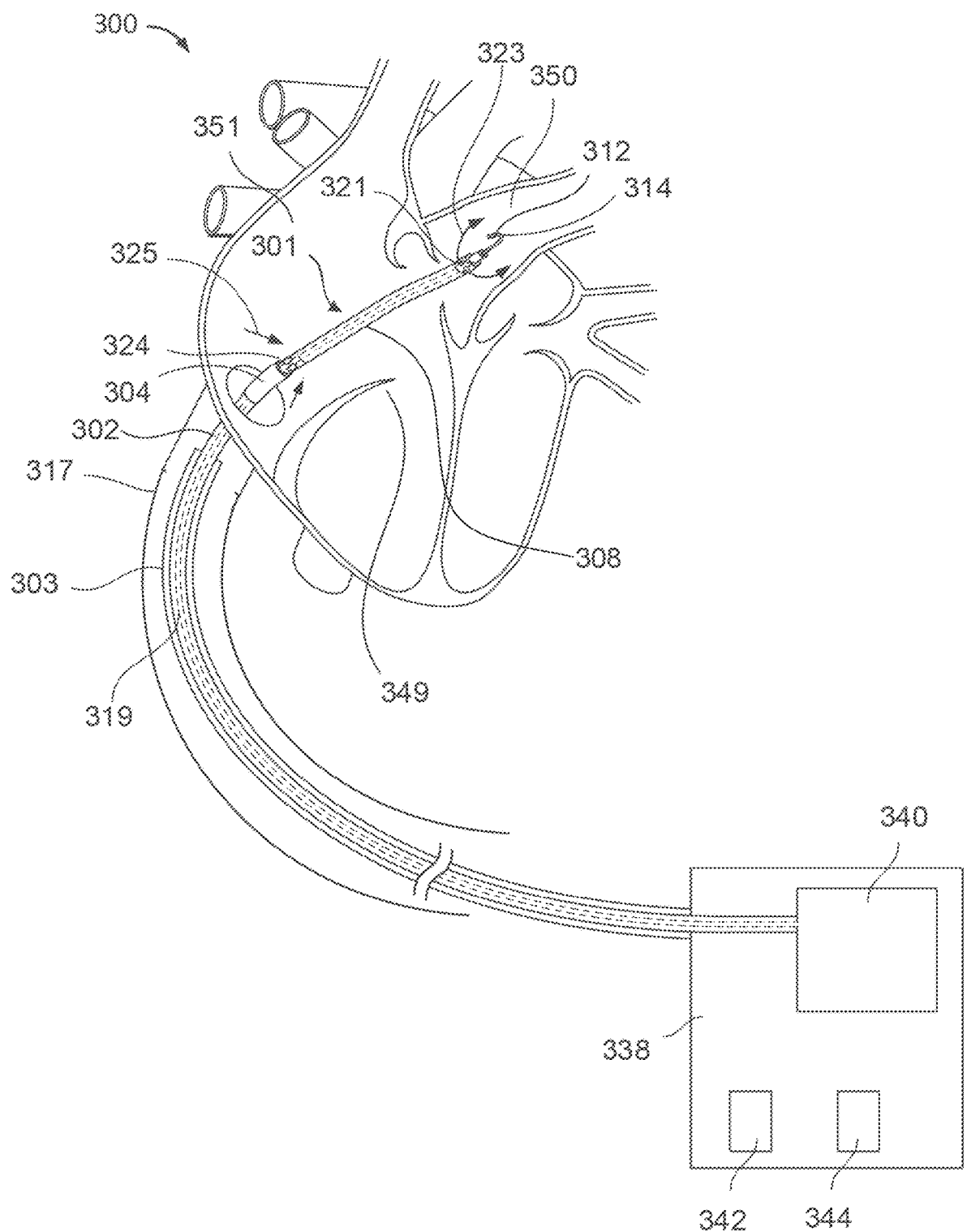
FIG. 3 shows an exemplary blood pump system including an electrode positioned in the right heart according to aspects of the disclosure.

The blood pump system including an electrode can also be used with a blood pump supporting the heart in a right-heart configuration. FIG. 3 shows an exemplary blood pump system 300 according to aspects of the disclosure which includes an electrode 312 positioned in the right heart and capable of measuring EKG signals and providing electrical charges to the heart for pacing and defibrillation. The blood pump system 300 includes a blood pump 301 and a controller 338.

The blood pump 301 includes a cannula 308, pump 304, at least one inlet aperture 324 through which blood flows into the cannula 308 (as indicated by arrows 325), at least one outlet aperture 321 through which blood exits the cannula 308 (as indicated by arrows 323), and a flexible projection 314 at a distal end of the cannula 308. For example, the blood pump 301 may be the blood pump system 100 of FIG. 1. The blood pump 301 may be an IMPELLA® device, or any other suitable blood pump. Similar to the above, the at least one inlet aperture 324 may be formed in the proximal end of cannula 308 or may be a formed in a pump housing structure attached to the proximal end of cannula 308. Likewise, the at least one outlet aperture 321 may be formed in the distal end of cannula 308 or may be formed in a blood outflow cage structure attached to the distal end of cannula 308 (which may be considered a part of cannula 308).

The pump 304 is coupled to a first catheter 302 extending through a second catheter 303. Both the first catheter 302 and the second catheter 303 extend through the vasculature to attach the blood pump 301 to the controller 338. For example, when the blood pump 301 is positioned in the right heart 351 so that the at least one inlet aperture 324 is in the inferior vena cava 317 and the at least one outlet aperture expels blood into the pulmonary artery 350, the electrode 312 is positioned within the pulmonary artery. The electrode 312 may be coupled to the cannula 308 of the blood pump 301, such that when the blood pump 301 is positioned in the right heart 351, the electrode 312 is positioned in the right ventricle 349. The electrode 312 can be placed on the cannula 308 and positioned in the right ventricle 349, on the flexible projection 314 (or the distal end or tip of the mechanical circulatory support system, if there is no flexible projection), or on the catheter 302 positioned near to the right heart 351 in the inferior vena cava 317. The portion of the cannula 308 positioned in the right ventricle 349 may be preferable, as it is closer to the myocardium. If the electrode 312 is not in the right ventricle 349, (for example if the electrode 312 is on the flexible projection 314) the blood pump 301 can be temporarily repositioned to place the electrode 312 in the right ventricle 349 before applying pacing or defibrillation.

The controller 338 includes a processor 340 (or set of one or more processors 340) for controlling operation of the blood pump and is which is communicatively coupled to the electrode 312. The controller also includes memory 342 and display 344 (which may further include one or more audio devices such as speakers, chimes, etc.). As described above, with regard to FIG. 2, the electrode 312 is coupled to the controller 338 by electrical wires 319 which provide the electrical connection and power supply from the controller 338 to the electrode 312. The electrode 312 transmits an EKG signal to the controller 338 which can be used by the controller to perform a number of tasks related to assessment of the patient's cardiac function, as described above. For example, the EKG signal can be used by the controller 338 to display the signal to a clinician, to extract cardiac parameters from the signal and other signals available to the controller 338, and to determine cardiac events or characteristics which indicate that pacing or defibrillation is required. When pacing or defibrillation is required, the controller 338 can sound an alarm and/or display a warning and/or recommendation to a clinician on the display 344, or can determine optimal settings and parameters for administration of an electric shock to the patient's heart as part of pacing or defibrillation and present the parameters to the clinician. The clinician then need only approve the recommended treatment to allow the electrode 312 to administer the electric shock to regulate the patient's heartbeat. As described above with regard to FIG. 2, the blood pump 301 may also include a reference electrode (not shown) positioned on the catheter 302. Pacing or defibrillation of the heart is provided by applying an electrical voltage between the electrode 312 and the reference electrode.

When the controller 338 extracts cardiac parameters from the signal and other signals available to the controller 338, these cardiac parameters can be presented to the clinician to aid in diagnosis and monitoring of the patient's health. Alternatively or additionally, the cardiac parameters can be used to determine whether a change in circulatory support being provided is recommended. The controller 338 may use the extracted cardiac parameters to determine if pump support should be increased or decreased. The controller 338 may make this determination and provide a recommendation to the clinician via the display 344, or the controller 338 may make the adjustment to the support provided by the blood pump 301 automatically. When the electrode 312 is positioned within the right ventricle 349, the EKG data provided by the electrode 312 can better reveal the condition of the right heart infarction. The EKG signal from the electrode 312 inside the right ventricle 349 may also better reveal cardiac conduction blockage in the right heart 351 than the electrode 312 placed on the left side of the heart. When these kinds of right heart conditions are detected, the EKG signal from the electrode 312 positioned within the right heart 351 enables a clinician to be better informed of the patient's condition and adjust treatments accordingly.

Incorporating the electrode 312 into the blood pump 301 enables faster detection and response to cardiac events, including arrhythmias requiring pacing or defibrillation as well as changes in cardiac function which require a change in the circulatory support provided by the blood pump 301.

Figure 4:
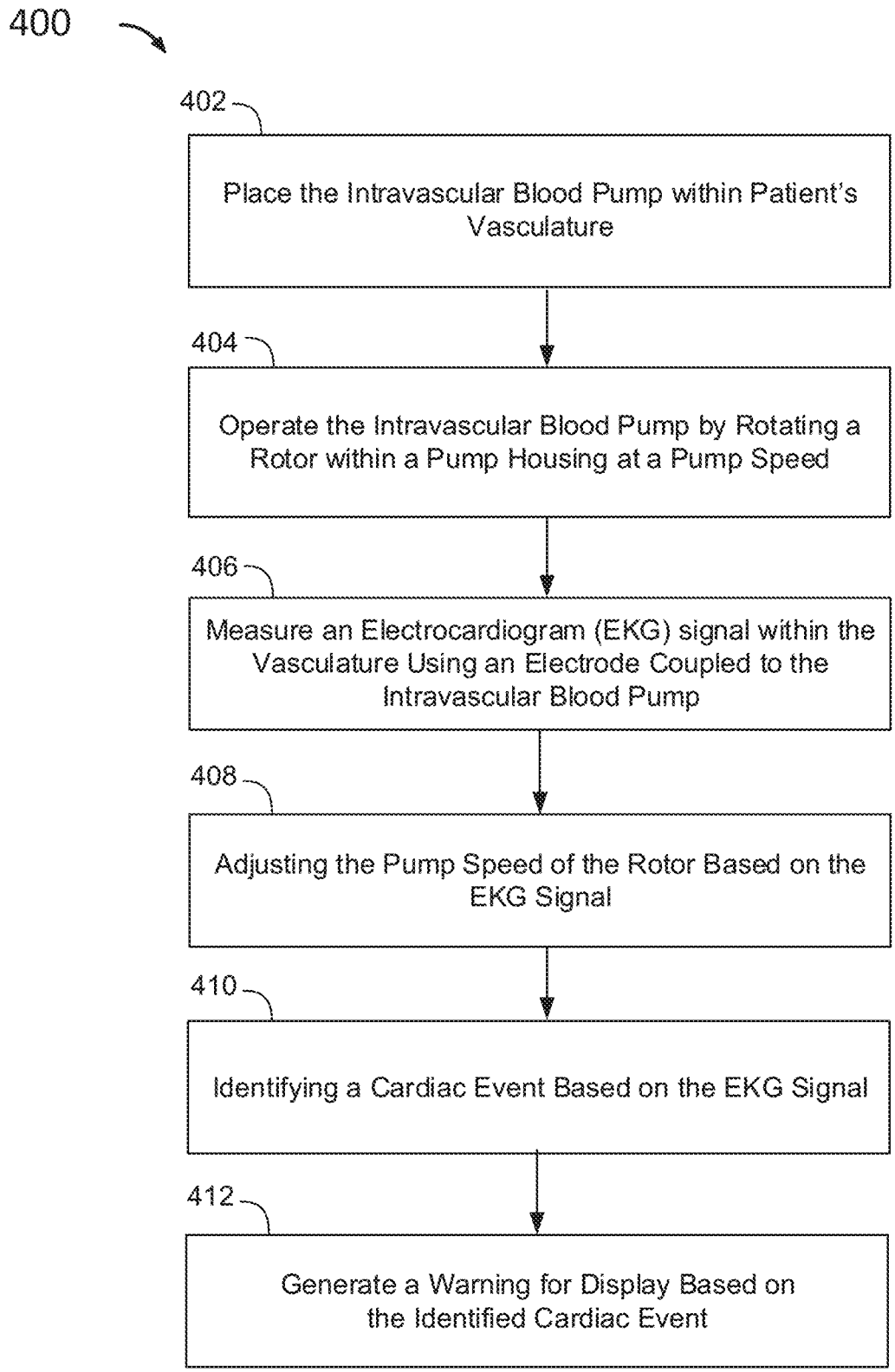
FIG. 4 shows a flow chart illustrating an exemplary method for operating an intravascular blood pump based on an EKG signal measured at an electrode coupled to the intravascular blood pump according to aspects of the disclosure.

FIG. 4 shows a flow chart illustrating an exemplary method 400 for operating an intravascular blood pump (e.g., blood pump system 100 of FIG. 1, blood pump 201 of FIG. 2, blood pump 301 of FIG. 3) based on an EKG signal measured at an electrode (e.g., electrode 112 of FIG. 1, electrode 212 of FIG. 2, electrode 312 of FIG. 3) coupled to the intravascular blood pump. The method described in FIG. 4 applies to intravascular blood pump systems (e.g., blood pump system 100 of FIG. 1, left-heart blood pump system 200 of FIG. 2, right-heart blood pump system 300 of FIG.

3). The method includes at step 402 placing the intravascular blood pump within the patient's vasculature, where the intravascular blood pump includes an electrode. The blood pump may be a left-heart blood pump positioned across the aortic valve such that the electrode is located within the left ventricle. Alternatively, the blood pump may be a right-heart blood pump positioned such that the electrode is located within the pulmonary artery. At step 404, the intravascular blood pump is operated by rotating the rotor within the pump housing at a pump speed. At step 406, the electrode coupled to the intravascular blood pump is used to measure an EKG signal within the vasculature. In some implementations, the EKG signal is used by a controller of the blood pump to extract other cardiac parameters indicative of cardiac function. For example, cardiac parameters may be directly determined from the EKG signal, or the EKG signal may be used in conjunction with other signals and data available to the controller, such as aortic pressure or motor current, to extract the cardiac parameters. The EKG signal may be used to determine a timing for another measurement, such as LVEDP.

At step 408, the pump speed of the rotor is adjusted based on the EKG signal. The pump speed of the rotor may be adjusted by the controller based on the EKG signal itself, or on the cardiac parameters determined from the EKG signal. The controller may determine, based on the EKG signal and other cardiac parameters, that the patient's cardiac health is improving and that the patient should be weaned from circulatory support. The controller may then automatically adjust the pump speed of the rotor to decrease the pump speed, or may alert a clinician that the patient should be weaned and prompt the clinician to manually adjust the rotor pump speed.

At step 410, a cardiac event is identified based on the EKG signal. The controller may include software for analyzing the EKG signal and determining a cardiac event, such as an irregular heartbeat, or a heartbeat which is too fast or too slow. The controller may further determine a method of treatment for the identified cardiac event. At step 412, a warning is generated for display based on the identified cardiac event. The controller may alert the clinician and display a notice that the cardiac event was detected. Further, the controller may display a recommendation for a method of treatment, and/or may prompt the clinician to administer the recommended method of treatment by the electrode coupled to the intravascular heart pump.

By incorporating the electrode with the intravascular blood pump, the signals detected by the electrode can be utilized by the blood pump in controlling operation of the blood pump, and can also be analyzed to provide clinicians with critical information about cardiac function and cardiac events much more quickly than may otherwise be available. Further, as described below with regard to FIGS. 5-8, because the electrode is already within the heart, the electrode can be used to provide treatment such as defibrillation and pacing of the heart with minimal delay.

Figure 5:
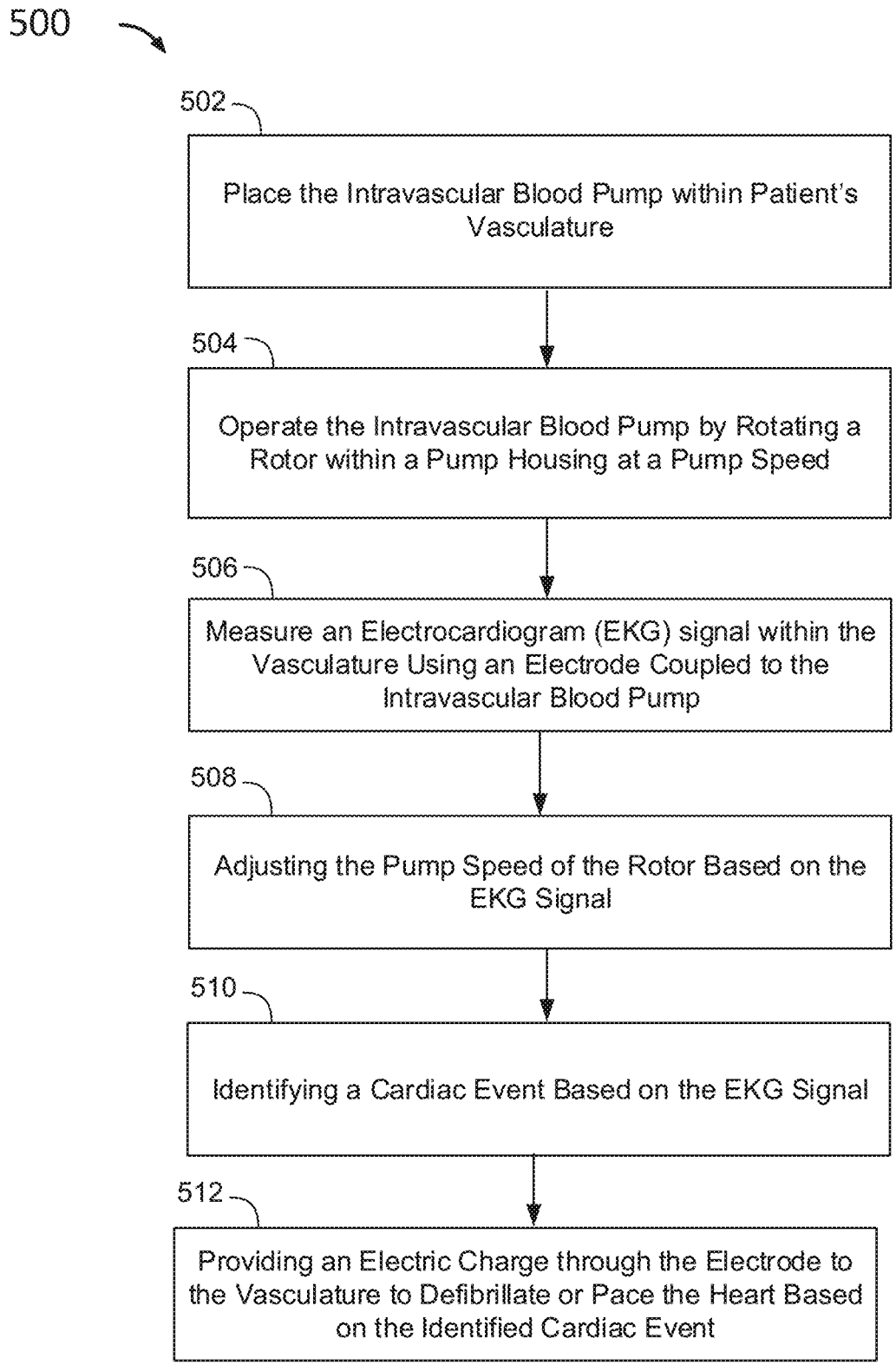
FIG. 5 shows a flow chart illustrating an exemplary method for providing cardiac support with an intravascular blood pump including an electrode according to aspects of the disclosure.

FIG. 5 shows a flow chart illustrating an exemplary method 500 for providing cardiac support with an intravascular blood pump (e.g., blood pump system 100 of FIG. 1, blood pump 201 of FIG. 2, blood pump 301 of FIG. 3) including an electrode (e.g., electrode 112 of FIG. 1, electrode 212 of FIG. 2, electrode 312 of FIG. 3). The method described in FIG. 5 applies to intravascular blood pump systems (e.g., blood pump system 100 of FIG. 1, left-heart blood pump system 200 of FIG. 2, right-heart blood pump system 300 of FIG. 3). At step 502, the intravascular blood pump is placed within the patient's vasculature. At step 504, the intravascular blood pump is operated by rotating a rotor within a pump housing at a pump speed. At step 506, the electrode coupled to the intravascular blood pump is used to measure an EKG signal in the vasculature. At step 508, the pump speed of the rotor is adjusted based on the EKG signal. At step 510, a cardiac event is identified based on the EKG signal. For example, the EKG signal may be analyzed to determine whether there are irregular heartbeats, or heartbeats which are too fast or too slow, requiring defibrillation or pacing to normalize the heartbeat. At step 512, an electric charge is provided through the electrode to the vasculature to defibrillate or pace the heart, based on the identified cardiac event.

While the methods of FIGS. 4 and 5 are described with regard to an intravascular blood pump coupled to an electrode, the methods can also be applied to any mechanical circulatory support device having an attached electrode, which may be placed into the vasculature surgically or by percutaneous insertion through the patient's vasculature. For example, the methods of FIGS. 4 and 5 are applicable to mechanical circulatory support devices such as IABPs, ECMO devices, LVADs implanted surgically, percutaneous expandable blood pumps, and intravascular blood pump systems positioned in the right or left heart.

Figure 6:
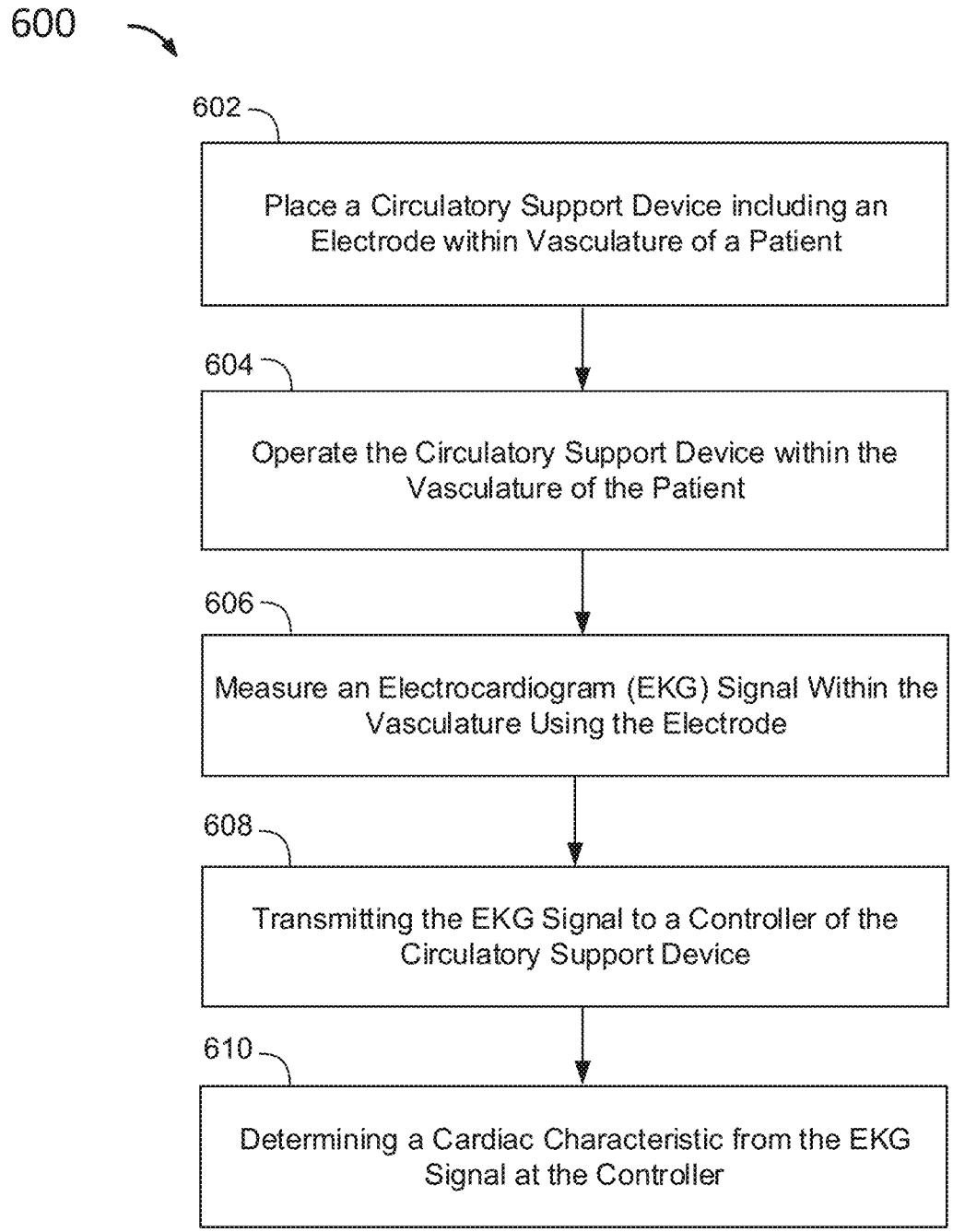
FIG. 6 shows a flow chart illustrating an exemplary method for measuring an EKG signal while providing circulatory support according to aspects of the disclosure.

FIG. 6 shows a flow chart illustrating an exemplary method 600 for measuring an EKG signal while providing circulatory support. The method described in FIG. 6 applies to any mechanical circulatory support device including IABPs, ECMO devices, LVADs, expandable blood pumps, and intravascular blood pumps (e.g., blood pump 201 of FIG. 2, blood pump 301 of FIG. 3) and blood pump systems (e.g., blood pump system 100 of FIG. 1, left-heart blood pump system 200 of FIG. 2, right-heart blood pump system 300 of FIG. 3). At step 602, a circulatory support device including an electrode (e.g., electrode 112 of FIG. 1, electrode 212 of FIG. 2, electrode 312 of FIG. 3) is placed within the vasculature of a patient. At step 604, the circulatory support device is operated within the vasculature of the patient. For example, the circulatory support device may be operated to pump blood through the patient's heart to provide continuous or pulsatile cardiac support. At step 606, an EKG signal is measured within the vasculature using the electrode, and at step 608, the EKG signal is transmitted to a controller of the circulatory support device.

At step 610, a cardiac characteristic is determined from the EKG signal by the controller. As an example, a cardiac characteristic extracted from the EKG signal may be a characteristic of the heartbeat, such as irregular beats, beats that are too slow or too fast, or skipping a beat. As another example, a timing for measurement of the LVEDP may be determined from the peak of the R-wave shown in the EKG signal, based on which an accurate LVEDP value can be measured. Other cardiac parameters and characteristics can be extracted from the EKG signal and other signals and information which may be available to the circulatory support device, such as pressure measurements, and pump or motor parameters. After the cardiac characteristic is determined, the cardiac characteristic may be displayed to a clinician, or may be used by the controller to determine and implement a method of treatment, such as administration of an electric shock to correct an irregular heartbeat, or a decrease in the level of circulatory support provided by the circulatory support device to wean a patient with improving cardiac function from support.

Figure 7:
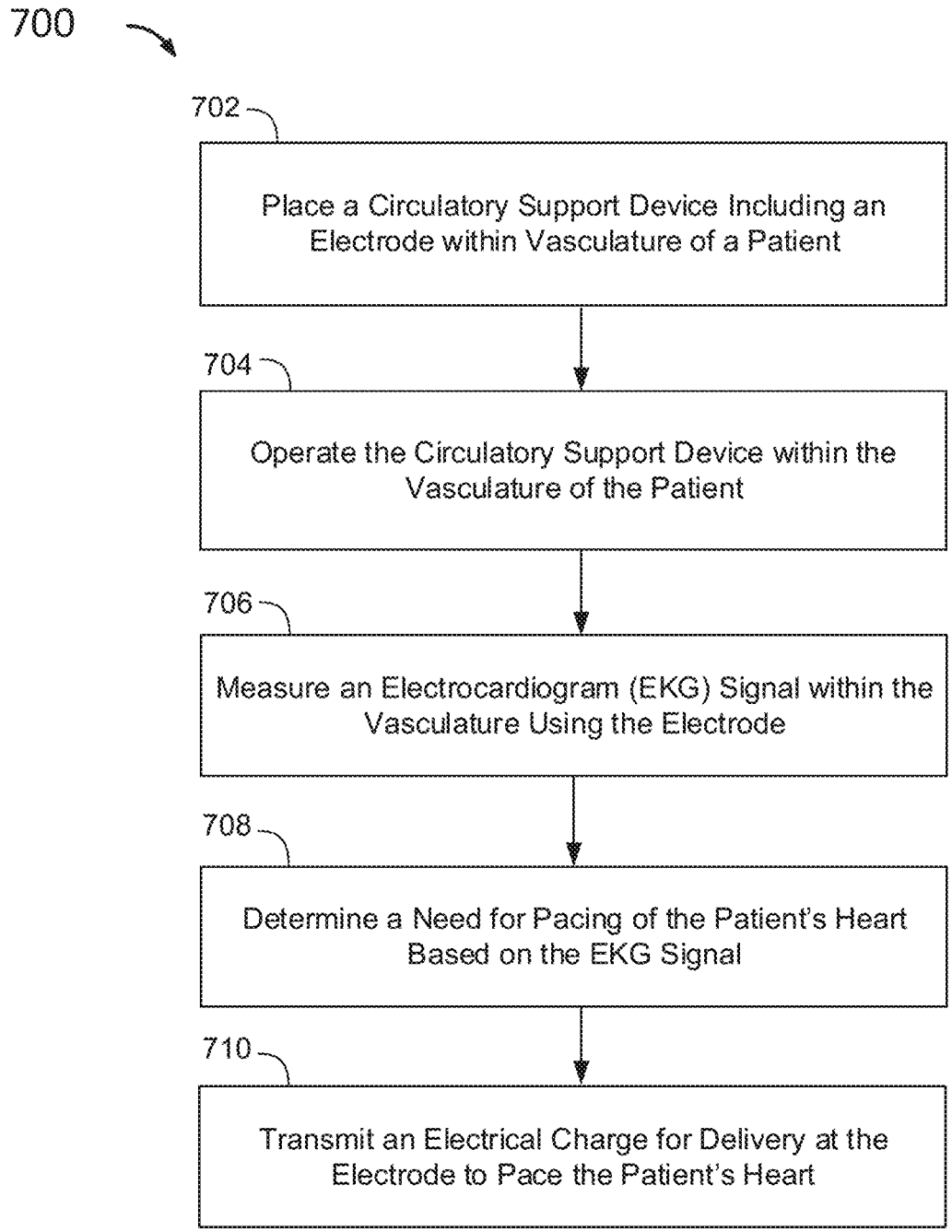
FIG. 7 shows a flow chart illustrating an exemplary method for providing pacing of a patient's heart according to aspects of the disclosure.

FIG. 7 shows a flow chart illustrating an exemplary method 700 for providing pacing of a patient's heart. The method described in FIG. 7 applies to any mechanical circulatory support device including IABPs, ECMO devices, LVADs, expandable blood pumps, and intravascular blood pumps (e.g., blood pump 201 of FIG. 2, blood pump 301 of FIG. 3) and blood pump systems (e.g., blood pump system 100 of FIG. 1, left-heart blood pump system 200 of FIG. 2, right-heart blood pump system 300 of FIG. 3). At step 702, a circulatory support device including an electrode (e.g., electrode 112 of FIG. 1, electrode 212 of FIG. 2, electrode 312 of FIG. 3) is placed within the vasculature of a patient. At step 704, the circulatory support device is operated within the vasculature of the patient. For example, the circulatory support device may be operated to pump blood through the patient's heart to provide continuous or pulsatile cardiac support. At step 706, an EKG signal is measured within the vasculature using the electrode.

At step 708, a need for pacing of the patient's heart is determined based on the EKG signal. For example, an abnormally slow heartbeat may indicate bradycardia and the need for regulation of the heart. The need for pacing may be determined by comparison of an EKG signal to a reference signal, comparing a current EKG signal to a historical EKG signal of the patient, or comparison of a number of heart beats per minute extracted from the EKG signal to a threshold, for example 60 beats per minute (BPM) for an adult. Alternatively, the abnormally slow heartrate may be determined by software programmed to identify bradycardia, or by a machine-learning algorithm trained to identify these events.

At step 710, an electrical charge is transmitted for delivery at the electrode to provide pacing to the patient's heart. The timing, current, heart rate and other parameters of the electrical charge may be input into a system by a clinician, or may be determined by a controller and approved by a clinician. The electrical charge is delivered at the electrode within the heart. Because the electrode is already in place and the charge can be delivered directly to the heart, the pacing of the heart using the circulatory support device including an electrode is more efficient and less dangerous than treatment using transcutaneous pacing.

Figure 8:
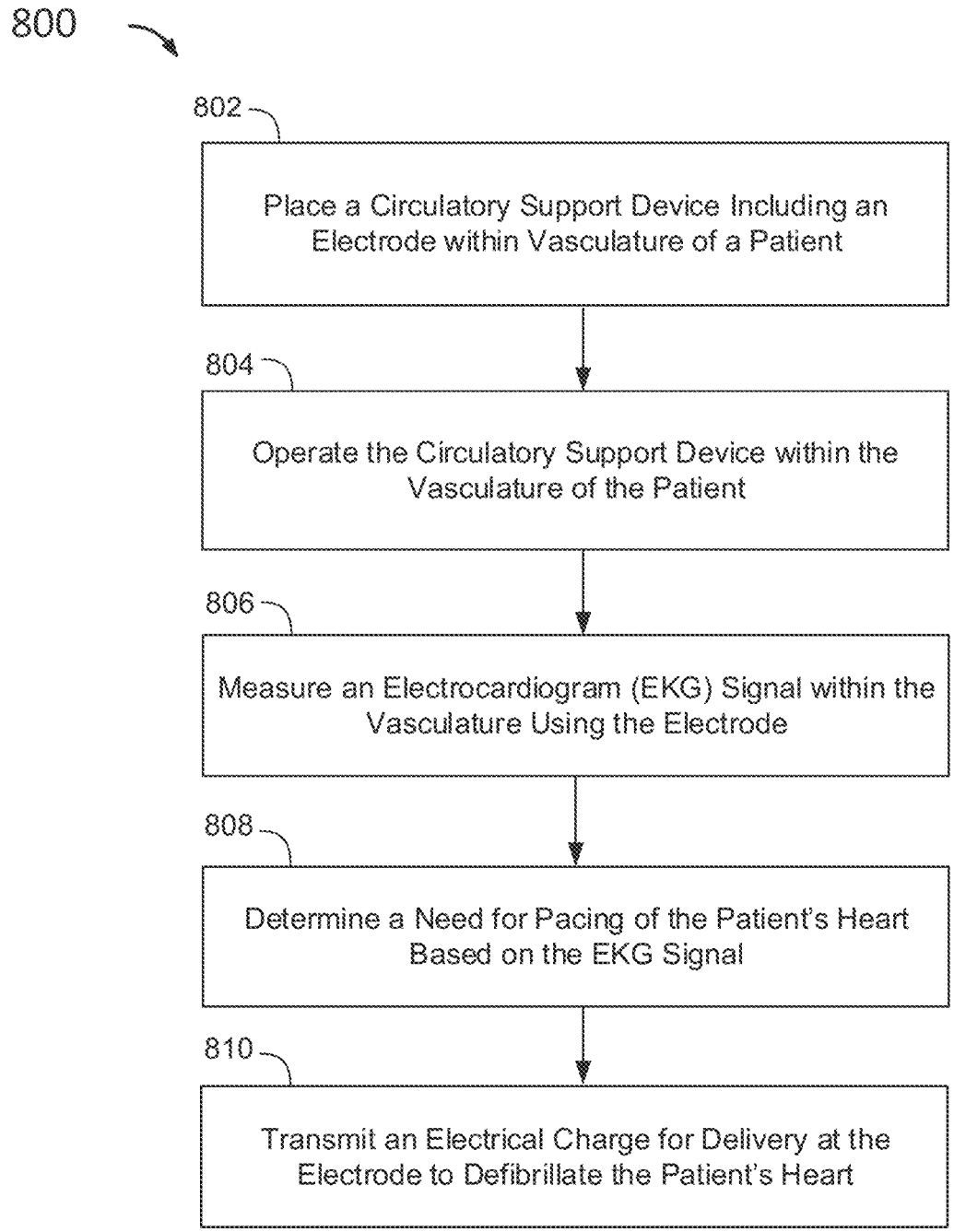
FIG. 8 shows a flow chart illustrating an exemplary method for providing defibrillation of a patient's heart according to aspects of the disclosure.

FIG. 8 shows a flow chart illustrating an exemplary method 800 for providing defibrillation of a patient's heart. The method described in FIG. 8 applies to any mechanical circulatory support device including IABPs, ECMO devices, LVADs, expandable blood pumps, and intravascular blood pumps (e.g., blood pump 201 of FIG. 2, blood pump 301 of FIG. 3) and blood pump systems (e.g., blood pump system 100 of FIG. 1, left-heart blood pump system 200 of FIG. 2, right-heart blood pump system 300 of FIG. 3). At step 802, a circulatory support device including an electrode (e.g., electrode 112 of FIG. 1, electrode 212 of FIG. 2, electrode 312 of FIG. 3) is placed within the vasculature of a patient. At step 804, the circulatory support device is operated within the vasculature of the patient. For example the circulatory support device may be operated to pump blood through the patient's heart to provide continuous or pulsatile cardiac support. At step 806, an EKG signal is measured within the vasculature using the electrode.

At step 808, a need for defibrillation of the patient's heart is determined based on the EKG signal. For example, an irregular heartbeat, or too fast of a heartbeat, may indicate cardiac dysrhythmia for which defibrillation is an appropriate treatment, such as ventricular fibrillation or pulseless ventricular tachycardia. The irregularity of the heartbeat may be determined by comparison of the EKG signal to a reference signal, comparison of a current EKG signal to a historical EKG signal of the patient, comparison of a number of heart beats per minute extracted from the EKG signal to a threshold value, or comparison of the EKG signal to a reference rhythm of heartbeats associated with cardiac arrest. Alternatively, the irregularity may be determined by software programmed to identify irregular or too fast heartbeats, or by a machine-learning algorithm trained to identify these events.

At step 810, an electrical charge is transmitted for delivery at the electrode to defibrillate the patient's heart. The timing and voltage of the electric shock may be input into a system by a clinician, or may be determined by a controller and approved by a clinician. The dose of electric current is then delivered to the heart through the electrode to depolarize the heart muscle and end the arrhythmia. Because the electrode is already in place and the charge can be delivered directly to the heart, defibrillation of the heart using the circulatory support device including an electrode is more efficient and less dangerous than treatment using a manual external defibrillator.

The foregoing description is merely intended to be illustrative of the principles of the technology. As such, the devices and methods described herein can be practiced by other than the described implementations, which are presented for purposes of illustration and not of limitation.

In addition, the disclosed features may be implemented in any combination or subcombination (including multiple dependent combinations and subcombinations) with one or more other features described herein. The various features described or illustrated above, including any components thereof, may also be combined or integrated into other systems. Moreover, certain features may be omitted or not implemented without departing from the spirit of the technology.

The systems and methods described may be implemented locally on a heart pump system or a controller of a heart pump system, such as the AIC. The heart pump system may comprise a data processing apparatus. The systems and methods described herein may be implemented remotely on a separate data processing apparatus. The separate data processing apparatus may be connected directly or indirectly to the heart pump system through cloud applications. The heart pump system may communicate with the separate data processing apparatus in real-time (or near real-time).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

EXEMPLARY IMPLEMENTATIONS

As already described, the systems and methods disclosed herein may be implemented in various ways. In that regard, the foregoing disclosure is intended to include, but not be limited to, the systems, methods, and combinations and subcombinations thereof that are set forth in the following categories of exemplary implementations.

Category A:
A1: A mechanical circulatory support system comprising:
a mechanical circulatory support device; and an electrode coupled to the mechanical circulatory support device.

A2: The mechanical circulatory support system of A1, wherein the mechanical circulatory support device is configured to be positioned at least in part in a patient's heart.

A3: The mechanical circulatory support system of A1 or A2, wherein the mechanical circulatory support device is one of an intravascular blood pump, an extracorporeal membrane oxygenation (ECMO) device, an intra aortic balloon pump, a left-ventricular assist device (LVAD) implanted surgically, or a percutaneous expandable blood pump positioned in the right or left heart.

A4: The mechanical circulatory support system of any of A1-A3, wherein the electrical signal from the electrode is an electrocardiogram (EKG) signal.

A5: The mechanical circulatory support system of any of A1-A4, wherein the electrode is configured to be positioned in the heart.

A6: The mechanical circulatory support system of any of A1-A5, wherein the electrode is communicatively coupled to a controller, and wherein the controller is configured to receive an electrical signal from the electrode.

A7: The mechanical circulatory support system of A6, wherein the controller is configured to control a level of support provided by the mechanical circulatory support device.

A8: The mechanical circulatory support system of A7, wherein the controller is configured to:
  process the electrical signal from the electrode; and
  generate for display the electrical signal from the electrode.

A9: The mechanical circulatory support system of A8, wherein the controller is configured to extract a left ventricular end diastolic pressure (LVEDP) from the EKG signal.

A10: The mechanical circulatory support system of A9, wherein the controller is configured to display the EKG signal and the LVEDP on a display.

A11: The mechanical circulatory support system of any of A6-A10, wherein the controller is configured to:
  store a historical LVEDP in a memory;
  compare a new LVEDP to the historical LVEDP accessed in the memory; and
  determine a difference between the new LVEDP and historical LVEDP.

A12: The mechanical circulatory support system of A11, wherein the controller is further configured to determine a support recommendation based on the difference between the new LVEDP and the historical LVEDP.

A13: The mechanical circulatory support system of A12, wherein the controller is configured to determine a support recommendation to increase support by the mechanical circulatory support device when the difference between the new LVEDP and the historical LVEDP is positive.

A14: The mechanical circulatory support system of A12, wherein the controller is configured to determine a support recommendation to decrease support when the difference between the new LVEDP and the historical LVEDP is negative.

A15: The mechanical circulatory support system of any of A12-A14, wherein the controller is further configured to generate for display the support recommendation.

A16: The mechanical circulatory support system of any of A12-A15, wherein the controller is further configured to automatically implement the support recommendation.

A17: The mechanical circulatory support system of any of A1-A16, further comprising a reference electrode coupled to the mechanical circulatory support device.

Category B:

B1: An intravascular blood pump system, comprising:
  a catheter having a proximal end and a distal end;
  a pump housing disposed distal of the distal end of the catheter;
  a rotor positioned at least partially in the pump housing; and
  an electrode coupled to a distal region of the blood pump.

B2: The intravascular blood pump of B1, further comprising:
  a flexible projection disposed distally of the pump housing.

B3: The intravascular blood pump of B1 or B2, wherein the electrode is positioned on the flexible projection.

B4: The intravascular blood pump of any of B1-B3, wherein the electrode is configured to function as a sensor.

B5: The intravascular blood pump of any of B1-B4, further comprising:
  a cannula coupled to the pump housing.

B6: The intravascular blood pump of B5, wherein the flexible projection is positioned on a distal end of the cannula.

B7: The intravascular blood pump of any of B1-B6, further comprising:
  a drive cable extending from the rotor through the catheter to the proximal end of the catheter, wherein the drive cable is configured to drive the rotor within the pump housing.

B8: The intravascular blood pump of any of B1-B7, further comprising:
  an electrical wire extending from the electrode through the catheter to the proximal end of the catheter.

B9: The intravascular blood pump of B8, wherein the electrical wire is embedded in a side wall of the pump housing.

B10: The intravascular blood pump of B8 or B10, wherein the electrical wire is configured to transmit a signal from the electrode to the proximal end of the catheter.

B11: The intravascular blood pump of any of B7-B10, wherein the electrical wire is configured to transmit an electrical charge from the proximal end of the catheter for delivery at the electrode.

B12: The intravascular blood pump of any of B1-B11, wherein the electrode is configured to be positioned within the heart.

B13: The intravascular blood pump of any of B1-B12, further comprising:
  a plurality of apertures formed in the pump housing; and
  a plurality of outlet apertures formed in the pump housing.

B14: The intravascular blood pump of B13, further comprising a reference electrode coupled to the catheter.

B15: The intravascular blood pump of B13 or B14, wherein the plurality of inlet apertures are configured to be positioned in a left ventricle of a heart, and wherein the outlet apertures are proximal of the inlet apertures and are configured to be positioned in an aorta of the heart.

B16: The intravascular blood pump of B15, wherein the electrode is configured to be positioned in the left ventricle.

B17: The intravascular blood pump of B16, wherein the electrode is configured to defibrillate the heart by transmitting an electric charge within the left ventricle.

B18: The intravascular blood pump of B16, wherein the electrode is configured to provide pacing to the heart by transmitting an electric charge within the left ventricle.

B19: The intravascular blood pump of B13, wherein the plurality of inlet apertures are configured to be positioned in an inferior vena cava of a heart, and wherein the plurality of outlet apertures are distal of the inlet apertures and are configured to be positioned in the pulmonary artery of the heart.

B20: The intravascular blood pump of B19, wherein the electrode is configured to be positioned in the right ventricle.

B21: The intravascular blood pump of B20, wherein the electrode is configured to defibrillate the heart by transmitting an electric charge within the right ventricle.

B22: The intravascular blood pump of B20, wherein the electrode is configured to provide pacing to the heart by transmitting an electric charge within the right ventricle.

B23: The intravascular blood pump of any of B1-B22, further comprising a pressure sensor coupled to the catheter.

Category C:

C1: A mechanical circulatory support system comprising:
a mechanical circulatory support device;
a controller communicatively coupled to the mechanical circulatory support device and configured to control a level of support provided by the mechanical circulatory support device; and
an electrode coupled to the mechanical circulatory support device.

C2: The mechanical circulatory support system of C1, wherein the electrode is communicatively coupled to the controller, and wherein the controller is configured to receive an electrical signal from the electrode.

C3: The mechanical circulatory support system of C2, wherein the controller is configured to:
process the electrical signal from the electrode; and
generate for display the electrical signal from the electrode.

C4: The mechanical circulatory support system of C2 or C3, wherein the electrical signal from the electrode is an electrocardiogram (EKG) signal.

C5: The mechanical circulatory support system of any of C1-C4, wherein the electrode is configured to be positioned in the heart.

C6: The mechanical circulatory support system of C4, wherein the controller is configured to extract a left ventricular end diastolic pressure (LVEDP) from the EKG signal.

C7: The mechanical circulatory support system of C6, wherein the controller is configured to display the EKG signal and the LVEDP on a display.

C8: The mechanical circulatory support system of C6 or C7, wherein the controller is configured to:
store a historical LVEDP in a memory;
compare a new LVEDP to the historical LVEDP accessed in the memory; and
determine a difference between the new LVEDP and historical LVEDP.

C9: The mechanical circulatory support system of C8, wherein the controller is further configured to determine a support recommendation based on the difference between the new LVEDP and the historical LVEDP.

C10: The mechanical circulatory support system of C9, wherein the controller is configured to determine a support recommendation to increase support when the difference between the new LVEDP and the historical LVEDP is positive.

C11: The mechanical circulatory support system of C9, wherein the controller is configured to determine a support recommendation to decrease support when the difference between the new LVEDP and the historical LVEDP is negative.

C12: The mechanical circulatory support system of any of C9-C11, wherein the controller is further configured to generate for display the support recommendation.

C13: The mechanical circulatory support system of any of C9-C12, wherein the controller is further configured to automatically implement the support recommendation.

C14: The mechanical circulatory support system of any of C9-C13, further comprising a reference electrode.

Category D:

D1: An intravascular blood pump system comprising:
an intravascular blood pump comprising:
a catheter having a proximal end and a distal end;
a pump housing disposed distal of the distal end of the catheter; and
a rotor positioned at least partially in the pump housing, the rotor configured to be rotatably driven;
a controller communicatively coupled to the intravascular blood pump and configured to control a level of support provided by the intravascular blood pump by controlling a speed of the rotor; and
an electrode coupled to the intravascular blood pump.

D2: The intravascular blood pump system of D1, further comprising:
a flexible projection disposed distally of the pump housing.

D3: The intravascular blood pump system of D1 or D2, wherein the electrode is positioned on the flexible projection.

D4: The intravascular blood pump system of any of D1-D3, wherein the electrode is configured to function as a sensor.

D5: The intravascular blood pump system of any of D1-D4, further comprising:
a cannula coupled to the pump housing.

D6: The intravascular blood pump system of D5, wherein the flexible projection is positioned on a distal end of the cannula.

D7: The intravascular blood pump system of any of D1-D6, further comprising:
a drive cable extending from the rotor through the catheter to the proximal end of the catheter, wherein the drive cable is configured to drive the rotor within the pump housing.

D8: The intravascular blood pump system of any of D1-D7, further comprising:
an electrical wire extending from the electrode through the catheter to the proximal end of the catheter.

D9: The intravascular blood pump system of D8, wherein the electrical wire is embedded in a side wall of the pump housing.

D10: The intravascular blood pump system of D8 or D9, wherein the electrode is communicatively coupled to the controller by the electrical wire, and wherein the controller is configured to receive an electrical signal from the electrode through the electrical wire.

D11: The intravascular blood pump system of any of D8-D10, wherein the controller is configured to:
process the electrical signal from the electrode; and
display the electrical signal from the electrode on a display.

D12: The intravascular blood pump system any of D8-D11, wherein the electrical signal from the electrode is an electrocardiogram (EKG) signal.

D13: The intravascular blood pump system of D12, wherein the controller is configured to extract a left ventricular end diastolic pressure (LVEDP) from the EKG signal.

D14: The intravascular blood pump system of D13, wherein the controller is configured to display at least one of the EKG signal and the LVEDP on a display.

D15: The intravascular blood pump system of D13 or D14, wherein the controller is configured to:
store a historical LVEDP in a memory;
compare a new LVEDP to the historical LVEDP accessed in the memory; and
determine a difference between the new LVEDP and historical LVEDP.

D16: The intravascular blood pump system of D15, wherein the controller is further configured to determine a support recommendation based on the difference between the new LVEDP and the historical LVEDP.

D17: The intravascular blood pump system of D16, wherein the controller is configured to determine a support recommendation to increase support when the difference between the new LVEDP and the historical LVEDP is positive.

D18: The intravascular blood pump system of D16, wherein the controller is configured to determine a support recommendation to decrease support when the difference between the new LVEDP and the historical LVEDP is negative.

D19: The intravascular blood pump system of any of D16-D18, wherein the controller is further configured to display the support recommendation on a display.

D20: The intravascular blood pump system of any of D16-D19, wherein the controller is further configured to automatically implement the support recommendation.

D21: The intravascular blood pump system of any of D13-D20, wherein the controller is further configured to determine a treatment recommendation based on the EKG signal.

D22: The intravascular blood pump system of any of D13-D20, wherein the controller is further configured to display an indication of the treatment recommendation on the display.

D23: The intravascular blood pump system of D22, further comprising a reference electrode coupled to the catheter.

D24: The intravascular blood pump system of D23, wherein the controller is configured to transmit an electrical charge for delivery at the electrode through the electrical wire to provide pacing of the heart or defibrillation of the heart in response to a user input.

D25: The intravascular blood pump system of D23, wherein the controller is configured to automatically transmit an electrical charge for delivery at the electrode through the electrical wire to provide pacing of the heart or defibrillation of the heart based on the treatment recommendation.

D26: The intravascular blood pump system of any of claims D1-D25, wherein the electrode is configured to be placed in the heart.

D27: The intravascular blood pump system of any of D1-D26, the intravascular blood pump further comprising:
a plurality of inlet apertures formed in the cannula; and
a plurality of outlet apertures formed in the pump housing.

D28: The intravascular blood pump system of D27, wherein the plurality of inlet apertures are configured to be positioned in a left ventricle of a heart, and wherein the outlet apertures are proximal of the inlet apertures and are configured to be positioned in an aorta of a heart.

D29: The intravascular blood pump system of D28, wherein the electrode is configured to be positioned in the left ventricle.

D30: The intravascular blood pump system of D29, wherein the electrode is configured to defibrillate the heart by transmitting an electric charge within the left ventricle.

D31: The intravascular blood pump system of D29, wherein the electrode is configured to provide pacing to the heart by transmitting an electric charge within the left ventricle.

D32: The intravascular blood pump system of D27, wherein the plurality of inlet apertures are configured to be positioned in an inferior vena cava of a heart, and wherein the plurality of outlet apertures are distal of the inlet apertures and are configured to be positioned in a pulmonary artery of the heart.

D33: The intravascular blood pump system of D32, wherein the electrode is configured to be positioned in the right ventricle.

D34: The intravascular blood pump system of D33, wherein the electrode is configured to transmit an electric charge within the right ventricle.

D35: The intravascular blood pump system of D33, wherein the electrode is configured to provide pacing to a heart by transmitting an electric charge within the right ventricle.

D36: The intravascular blood pump system of any of D1-D35, further comprising a pressure sensor coupled to the catheter.

Category E:

E1: A method of providing circulatory support with an intravascular blood pump, the method comprising:
placing the intravascular blood pump within vasculature of a patient;
operating the intravascular blood pump by rotating a rotor of the intravascular blood pump within a pump housing at a pump speed;
measuring an electrocardiogram (EKG) signal within the vasculature using an electrode coupled to the intravascular blood pump; and
adjusting the pump speed of the rotor based on the EKG signal.

E2: The method of E1, wherein placing the intravascular blood pump within vasculature of a patient further comprises placing the intravascular blood pump into a heart of a patient such that the electrode is positioned in the heart.

E3: The method of E2, further comprising:
generating for display the EKG signal; and
receiving a user input to adjust the pump speed.

E4: The method of E3, further comprising:
generating for display a recommendation to adjust the pump speed based on the EKG signal.

E5: The method of E1-E4, further comprising: calculating a left ventricular end diastolic pressure (LVEDP) from the EKG signal.

E6: The method of E5, further comprising:
determining a recommendation to adjust the pump speed based on the LVEDP calculated from the EKG signal.

E7: The method of E6, wherein determining a recommendation to adjust the pump speed further comprises:
accessing a historical LVEDP of the patient;
comparing a current LVEDP of the patient with the historical LVEDP; and
determining a difference between the current LVEDP and the historical LVEDP.

E8: The method of E7, further comprising:
determining a recommendation to increase pump speed when the difference between the current LVEDP and the historical LVEDP is positive.

E9: The method of E7, further comprising:
determining a recommendation to decrease pump speed when the difference between the current LVEDP and the historical LVEDP is negative.

E10: The method of E1-E9, further comprising:
determining a recommendation to provide pacing of the heart based on the EKG signal;
generating for display the recommendation to provide pacing of the heart to a user; and
transmitting an electrical charge for delivery at the electrode to pace the heart of the patient in response to a received input from the user.

E11: The method of E10, wherein transmitting an electrical charge for delivery at the electrode to pace the heart further comprises delivering an electrical voltage between a reference electrode and the electrode.

E12: The method of E1-E9, further comprising:
determining a recommendation to provide defibrillation of the heart based on the EKG signal;
generating for display the recommendation to provide defibrillation of the heart to a user; and
transmitting an electrical charge for delivery at the electrode to defibrillate the heart of the patient in response to a received input from the user.

E12: The method of E11, wherein transmitting an electrical charge for delivery at the electrode to defibrillate the heart further comprises delivering an electrical voltage between a reference electrode and an electrode.

E13: The method of E1-E12, wherein placing the intravascular blood pump within vasculature of a patient further comprises positioning the intravascular blood pump within the vasculature such that the electrode coupled to the intravascular blood pump is within a left ventricle.

E14: The method of E1-E12, wherein placing the intravascular blood pump within vasculature of a patient further comprises positioning the intravascular blood pump within the vasculature such that the electrode coupled to the intravascular blood pump is within a right ventricle.

Category F:

F1: A method for measuring an EKG signal while providing circulatory support, the method comprising:
placing a circulatory support device within vasculature of a patient, the circulatory support device including an electrode coupled to the circulatory support device;
operating the circulatory support device within the vasculature of the patient; and
measuring an electrocardiogram (EKG) signal within the vasculature using the electrode.

F2: The method of F1, wherein the circulatory support device is an intravascular blood pump.

F3: The method of F1 or F2, wherein placing a circulatory support device within vasculature of the patient further comprises placing the circulatory support device within a heart of the patient such that the electrode is positioned in the heart.

F4: The method of any of F1-F3, further comprising:
transmitting the EKG signal to a controller coupled to the circulatory support device.

F5: The method of F4, further comprising:
generating for display the EKG signal.

F6: The method of F4 or F5, further comprising:
storing the EKG signal in a memory of the controller as a historical EKG signal.

F7: The method of any of F4-F6, further comprising:
calculating a left ventricular end-diastolic pressure (LVEDP) from the EKG signal; and
storing the LVEDP in a memory of the controller as a historical LVEDP signal.

F8: The method of F6 or F7, further comprising:
determining a treatment recommendation based on a comparison of the historical LVEDP and a current LVEDP.

F9: The method of F8, further comprising:
generating for display the treatment recommendation to a user.

F10: The method of F8, further comprising:
automatically performing the treatment recommendation.

F11: The method of any of F8-F10, further comprising:
determining a recommendation to increase support provided by the circulatory support device when the current LVEDP is higher than the historical LVEDP; and
determining a recommendation to decrease support provided by the circulatory support device when the current LVEDP is lower than the historical LVEDP.

Category G:

G1: A method for providing pacing of a patient's heart while providing circulatory support, the method comprising:
placing a circulatory support device within vasculature of a patient, the circulatory support device including an electrode coupled to the circulatory support device;
operating the circulatory support device within the vasculature;
measuring an electrocardiogram (EKG) signal within the vasculature using the electrode;
determining a need for pacing of the patient's heart based on the EKG signal; and
transmitting an electrical charge for delivery at the electrode to pace the patient's heart.

G2: The method of G1, wherein the circulatory support device is an intravascular blood pump.

G3: The method of G1 or G2, wherein placing a circulatory support device within vasculature of the patient further comprises placing the circulatory support device within a heart of the patient such that the electrode is positioned in the heart.

G4: The method of any of G1-G3, further comprising:
transmitting the EKG signal to a controller coupled to the circulatory support device.

G5: The method of G4, further comprising:
generating for display the EKG signal.

G6: The method of G4 or G5, further comprising:
storing the EKG signal in a memory of the controller as a historical EKG signal.

G7: The method of G6, wherein determining a need for pacing of a patient's heart further comprises comparison of the historical EKG signal to a current EKG signal.

G8: The method of any of G1-G6, wherein determining a need for pacing of a patient's heart further comprises:
extracting of EKG signal characteristics from a current EKG signal; and
comparing of the EKG signal characteristics to one or more thresholds.

G9: The method of G6, wherein determining a need for pacing of a patient's heart further comprises:
extracting EKG signal characteristics from the current EKG signal and from the historical EKG signal; and
comparing the current EKG signal characteristics to the historical EKG characteristics.

G10: The method of any of G1-G9, wherein transmitting an electrical charge for delivery at the electrode to pace the patient's heart comprises:

transmitting one or more electrical charges for delivery to the heart to increase a heart rate.

G11: The method of any of G1-G10, wherein placing a circulatory support device within vasculature of a patient further comprises:

placing the circulatory support device within vasculature of the patient such that the electrode coupled to the circulatory support device is positioned in one of a left ventricle or right ventricle.

G12: The method of any of G1-G11, wherein transmitting an electrical charge for delivery at the electrode to pace the patient's heart further comprises transmitting an electrical voltage between the electrode and a reference electrode.

Category H:

H1: A method for providing defibrillation of a patient's heart while providing circulatory support, the method comprising:

placing a circulatory support device within vasculature of a patient, the circulatory support device including an electrode coupled to the circulatory support device;

operating the circulatory support device within the vasculature; and measuring an electrocardiogram (EKG) signal within the vasculature using the electrode;

determining a need for defibrillation of the patient's heart based on the EKG signal; and transmitting an electrical charge for delivery at the electrode to defibrillate the patient's heart.

H2: The method of H1, wherein the circulatory support device is an intravascular blood pump.

H3: The method of H1 or H2, wherein placing a circulatory support device within vasculature of the patient further comprises placing the circulatory support device within a heart of the patient such that the electrode is positioned in the heart.

H4: The method of any of H1-H3, further comprising:

transmitting the EKG signal to a controller coupled to the circulatory support device.

H5: The method of H4, further comprising:

generating for display the EKG signal.

H6: The method of H4 or H5, further comprising:

storing the EKG signal in a memory of the controller as a historical EKG signal.

H7: The method of H6, wherein determining a need for pacing of a patient's heart further comprises comparison of the historical EKG signal to a current EKG signal.

H8: The method of any of H1-H6, wherein determining a need for defibrillation of a patient's heart further comprises:

extracting of EKG signal characteristics from a current EKG signal; and comparing of the EKG signal characteristics to one or more thresholds.

H9: The method of H6, wherein determining a need for defibrillation of a patient's heart further comprises:

extracting EKG signal characteristics from the current EKG signal and from the historical EKG signal; and comparing the current EKG signal characteristics to the historical EKG characteristics.

H10: The method of any of H1-H9, wherein transmitting an electrical charge for delivery at the electrode to defibrillate the patient's heart comprises:

transmitting one or more electrical charges for delivery to the heart to restart function of the heart.

H11: The method of any of H1-H10, wherein placing a circulatory support device within vasculature of a patient further comprises:

placing the circulatory support device within vasculature of the patient such that the electrode coupled to the circulatory support device is positioned in one of a left ventricle or right ventricle.

H12: The method of any of H1-H11, wherein transmitting an electrical charge for delivery at the electrode to defibrillate the patient's heart further comprises transmitting an electrical voltage between the electrode and a reference electrode.

The invention claimed is:

1. An intravascular blood pump system comprising:
an intravascular blood pump comprising:
a catheter having a proximal end and a distal end;
a pump housing coupled to the distal end of the catheter;
a rotor positioned at least partially in the pump housing, the rotor configured to be rotatably driven; and
a cannula coupled to the pump housing; and
an electrode mounted on the intravascular blood pump such that the electrode is positioned within a patient's heart when the intravascular blood pump is positioned within vasculature of the patient, wherein the electrode is configured to sense an electrocardiogram (EKG) signal of the patient's heart and to transmit an electric charge to the patient's heart to provide pacing or defibrillation of the patient's heart.

2. The intravascular blood pump system of claim 1, further comprising:
a controller communicatively coupled to the intravascular blood pump and the electrode, and configured to control a level of support provided by the intravascular blood pump by controlling a speed at which the rotor is rotatably driven.

3. The intravascular blood pump system of claim 2, wherein the controller is further configured to:
process the EKG signal from the electrode; and
determine a left ventricular end diastolic pressure (LVEDP) based on the EKG signal.

4. The intravascular blood pump system of claim 3, wherein the controller is further configured to display at least one of the EKG signal and the LVEDP on a display.

5. The intravascular blood pump system of claim 2, wherein the controller is further configured to:
process a first EKG signal from the electrode;
determine a first LVEDP based on the first EKG signal;
store the first LVEDP in memory;
process a second EKG signal from the electrode;
determine a second LVEDP based on the first EKG signal;
compare the second LVEDP to the first LVEDP accessed in the memory; and
determine a difference between the second LVEDP and the first LVEDP.

6. The intravascular blood pump system of claim 5, wherein the controller is further configured to determine a support recommendation for the intravascular blood pump based on the difference between the second LVEDP and the first LVEDP.

7. The intravascular blood pump system of claim 6, wherein the controller is further configured to determine a support recommendation to increase the support provided by the intravascular blood pump when the difference between the second LVEDP and the first LVEDP is positive.

8. The intravascular blood pump system of claim 6, wherein the controller is further configured to determine a support recommendation to decrease the support provided by the intravascular blood pump when the difference between the second LVEDP and the first LVEDP is negative.

9. The intravascular blood pump system of claim 6, wherein the controller is further configured to display the support recommendation on a display.

10. The intravascular blood pump system of claim 6, wherein the controller is further configured to automatically implement the support recommendation by adjusting the speed at which the rotor is rotatably driven.

11. The intravascular blood pump system of claim 2, wherein the controller is further configured to:
process the EKG signal from the electrode; and
determine a recommendation to provide pacing or defibrillation of the patient's heart based on the EKG signal.

12. The intravascular blood pump system of claim 11, wherein the controller is further configured to determine the recommendation based at least in part on whether the EKG signal indicates that the patient is experiencing an irregular heartbeat.

13. The intravascular blood pump system of claim 11, wherein the controller is further configured to display the recommendation on a display.

14. The intravascular blood pump system of claim 2, wherein the controller is further configured to control the electrode to produce the electric charge within the patient's heart to provide pacing or defibrillation of the patient's heart.

15. The intravascular blood pump system of claim 1, wherein the intravascular blood pump further comprises a flexible projection coupled to a distal end of the cannula, and wherein the electrode is positioned on the flexible projection.

16. The intravascular blood pump system of claim 1, wherein the intravascular blood pump further comprises a drive cable extending from the rotor through the catheter to the proximal end of the catheter, the drive cable being configured to rotatably drive the rotor.

17. The intravascular blood pump system of claim 1, wherein the intravascular blood pump further comprises a motor positioned within the pump housing, the motor configured to rotatably drive the rotor.

18. The intravascular blood pump system of claim 1, further comprising a reference electrode mounted to the intravascular blood pump proximally of the electrode.

19. A method of providing pacing or defibrillation of a patient's heart while providing circulatory support to the patient with an intravascular blood pump, the method comprising:
controlling, by one or more processors of a controller, an intravascular blood pump to pump at a first pump speed;
receiving, by the one or more processors, an electrocardiogram (EKG) signal of the patient's heart from an electrode mounted to the intravascular blood pump, wherein the electrode is mounted to the intravascular blood pump such that the electrode is positioned within the patient's heart when the intravascular blood pump is positioned within the vasculature of the patient; and
controlling, by the one or more processors, the electrode to produce an electric charge within the patient's heart to provide pacing or defibrillation of the patient's heart.

20. The method of claim 19, further comprising, determining, by the one or more processors, a need for pacing or defibrillation of the patient's heart based on the EKG signal.

\* \* \* \* \*